US011020599B2

(12) United States Patent
McSherry et al.

(10) Patent No.: US 11,020,599 B2
(45) Date of Patent: Jun. 1, 2021

(54) IMPLANTABLE LEAD INTERCONNECT SYSTEM HAVING A ROTATING CAM

(71) Applicant: Heraeus Medical Components LLC, St. Paul, MN (US)

(72) Inventors: Paul McSherry, Woodbury, MN (US); Stephen K. Sundquist, Minnetonka, MN (US); Steven E. Scott, St. Paul, MN (US); Randall S. Nelson, Pine Springs, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 16 days.

(21) Appl. No.: 16/478,648

(22) PCT Filed: Jan. 18, 2018

(86) PCT No.: PCT/US2018/014157
§ 371 (c)(1),
(2) Date: Jul. 17, 2019

(87) PCT Pub. No.: WO2018/136595
PCT Pub. Date: Jul. 26, 2018

(65) Prior Publication Data
US 2019/0366101 A1     Dec. 5, 2019

Related U.S. Application Data

(60) Provisional application No. 62/448,176, filed on Jan. 19, 2017.

(51) Int. Cl.
*H01R 13/502*     (2006.01)
*A61N 1/375*     (2006.01)
(Continued)

(52) U.S. Cl.
CPC ............ *A61N 1/3752* (2013.01); *A61N 1/05* (2013.01); *H01R 13/62905* (2013.01);
(Continued)

(58) Field of Classification Search
CPC .. A61N 1/3752; A61N 1/05; H01R 13/62905; H01R 24/58; H01R 2107/00; H01R 2201/12
(Continued)

(56) References Cited

U.S. PATENT DOCUMENTS 3,372,367 A * 3/1968 Concannon ............ H01R 24/58
439/864
5,560,358 A * 10/1996 Arnold ............... A61B 5/04001
600/373
(Continued)

OTHER PUBLICATIONS

International Search Report and Written Opinion dated Jul. 26, 2018 in parallel PCT Application No. PCT/US2018/014157.

*Primary Examiner* — Hae Moon Hyeon
(74) *Attorney, Agent, or Firm* — Dicke, Billig & Czaja, PLLC

(57) ABSTRACT

One aspect is a medical lead interconnect system. The medical lead interconnect system is configured to selectively electrically couple a linear array of contact rings of an implantable medical lead to an electrical outlet coupling. The medical lead interconnect system includes a housing with an electrical outlet, a pair of plates position within the housing and has a plurality of connector pins, a biasing member configured bias the pair of plates toward one another, and a cam configured to rotate between an open position in which the pair of plates are biased towards one another, and a closed position in which the pair plates are forced apart.

19 Claims, 8 Drawing Sheets

(51) Int. Cl.
*A61N 1/05* (2006.01)
*H01R 13/629* (2006.01)
*H01R 24/58* (2011.01)
*H01R 24/60* (2011.01)
*H01R 107/00* (2006.01)

(52) U.S. Cl.
CPC ............ *H01R 24/58* (2013.01); *H01R 24/60* (2013.01); *H01R 2107/00* (2013.01); *H01R 2201/12* (2013.01)

(58) Field of Classification Search
USPC .......................... 607/115; 439/668, 864, 909
See application file for complete search history.

(56) References Cited

U.S. PATENT DOCUMENTS

| | | | | |
|---|---|---|---|---|
| 5,766,042 | A * | 6/1998 | Ries | H01R 24/28 |
| | | | | 439/668 |
| 6,154,678 | A | 11/2000 | Lauro | |
| 6,162,101 | A | 12/2000 | Fischer et al. | |
| 6,671,534 | B2 * | 12/2003 | Putz | A61B 5/04 |
| | | | | 439/885 |
| 7,690,953 | B2 * | 4/2010 | Boyd | H01R 24/58 |
| | | | | 439/717 |
| 8,548,601 | B2 * | 10/2013 | Chinn | A61N 1/3752 |
| | | | | 607/116 |
| 2003/0050549 | A1 * | 3/2003 | Sochor | A61N 1/0529 |
| | | | | 600/378 |
| 2012/0135624 | A1 | 5/2012 | Putz | |
| 2015/0303609 | A1 | 10/2015 | Barker | |
| 2016/0136435 | A1 | 5/2016 | Calderon et al. | |

* cited by examiner

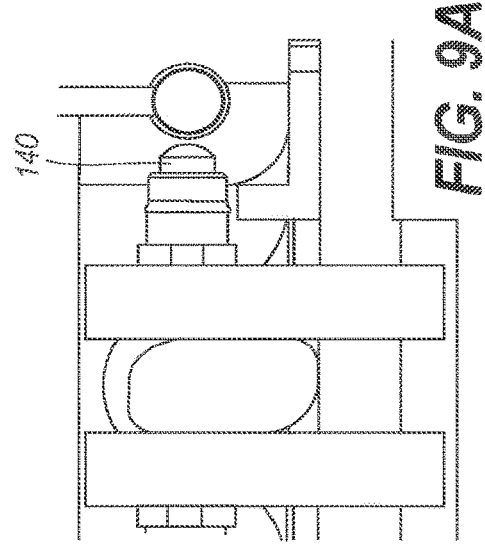
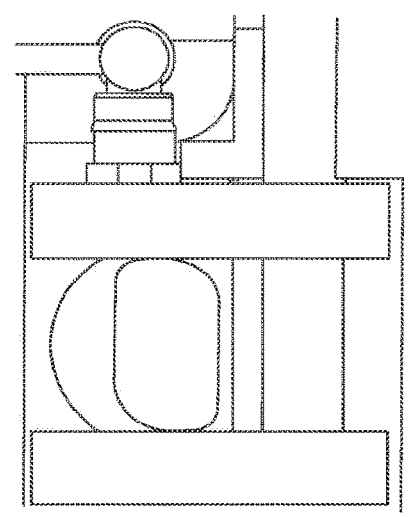
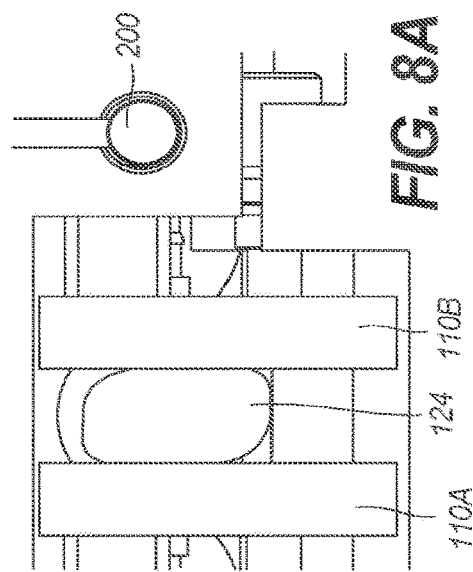
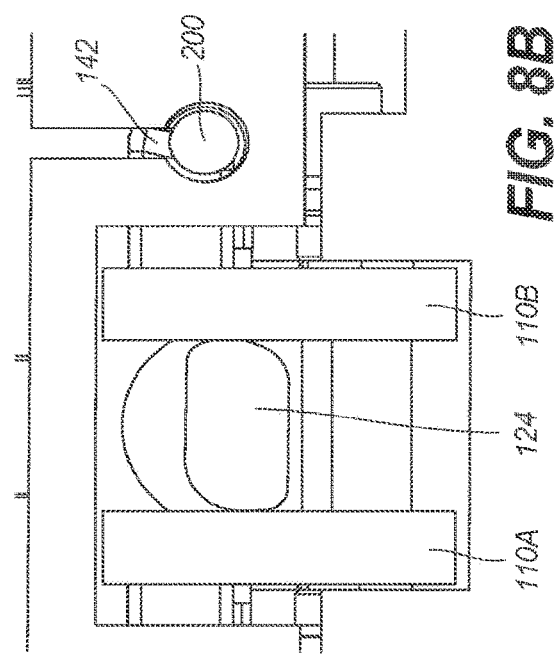

IMPLANTABLE LEAD INTERCONNECT SYSTEM HAVING A ROTATING CAM

RELATED APPLICATION INFORMATION

This application claims the benefit of U.S. Provisional Application No. 62/448,176, filed Jan. 19, 2017, the contents of which are fully incorporated herein by reference.

TECHNICAL FIELD

The present disclosure relates generally to electrical connectors for use in the medical field. More particularly, the present disclosure relates to medical connectors for implantable multi-contact medical electrode or electrical conduction devices.

BACKGROUND

Medical devices with neural interface capabilities are generally configured to provide an interconnection between the neuromuscular tissue of a patient and one or more recording, monitoring, control and/or stimulation systems. Notable neuro-stimulation systems include cardiac pacemakers, defibrillation systems, cochlear implants, deep brain stimulation systems, gastric stimulation systems, vagal nerve stimulation systems, and phrenic nerve stimulation systems. Functional electrical stimulation systems have also been applied to restore some functionality paralyzed extremities and spinal cord injury patients.

One of the more common types of neuro-stimulation is often referred to as spinal cord stimulation, and is used to treat chronic nerve pain in patients. A typical spinal cord stimulation device is comprised of a small stimulator or generator in electrical communication with one or more electrodes called leads. The leads are implanted into the epidural space near a patient's spine. The generator produces mild electrical pulses, which interfere with the nerve generated pain signals before they reach the patient's brain, thereby replacing the pain normally experienced by the patient with a tingling sensation.

In many neuro-stimulation systems, the leads exit the patient for connection to an external medical device. For example, with spinal cord stimulation, it is common practice to test and calibrate the leads prior to implanting an implantable stimulation unit into the patient's body. After implanting the leads, for example in the epidural space, their efficacy is tested over a period of multiple days by using an external stimulator. After the trial period is over, if the leads function as intended, the external stimulator can be replaced by an implantable stimulator that is programmed appropriately.

The leads may be in the form of an insulated electrically conductive wire having a distal end for insertion into a patient, and a proximal end for connection to a medical device. In order to be inserted into a patient, the leads must generally be narrow in diameter. For example, in some cases the leads must be capable of insertion through an epidural needle. One such type of lead measures 1.3 mm in diameter. The proximal end of the leads can include a plurality of spaced apart electrical contacts for connection to a medical device. For example, one type of lead has a linear array of eight contact rings.

Presently, manufacturers of neuro-stimulation medical devices must incorporate a mechanical coupling which functions to couple the leads to the medical device. This mechanical coupling, which in addition to requiring moving parts, must be both compact and reliable. As a result, design of such mechanical couplings may divert development time and costs which would otherwise be spent on the neuro-stimulation, controlling or monitoring aspects of the medical device.

SUMMARY OF THE DISCLOSURE

Embodiments of the present disclosure provide an implantable medical lead interconnect system designed to help neuro-stimulation companies save development time and costs, by providing a prefabricated electrical connection between one or more implantable medical lead and an electrical outlet coupling. In some embodiments, the electrical outlet coupling can be a standardized 8- or 16-pin/receptacle electrical outlet coupling, the corresponding mating plug of which can be more easily incorporated into the design of a medical device, such an external stimulator, controller or monitor, for selective connection to the electrical outlet coupling. In one embodiment, the implantable medical lead interconnect system is designed to facilitate an electrical connection between a single implantable medical lead and the electrical outlet coupling. In another embodiment, the implantable medical lead interconnect system is designed to facilitate in electrical connection between a pair of implantable medical leads and the electrical outlet coupling. The electrical connection of more than two implantable medical leads with the electrical outlet coupling is also contemplated.

One embodiment of the present disclosure provides a medical lead interconnect system configured to selectively electrically couple a linear array of contact rings of an implantable medical lead to an electrical outlet coupling. The medical lead interconnect system can include a housing, a pair of plates, a biasing member, and a cam. The housing can include an electrical outlet coupling. The pair of plates can be positioned within the housing, and each plate can have a plurality of connector pins. The biasing member can be configured to bias the pair of plates towards one another. The cam can be configured to rotate between an open position in which the pair of plates are biased towards one another, and a closed position in which the pair plates are forced apart. Each of the connector pins can correspond to a contact ring of the linear array of contact rings of the medical lead to selectively create an electrical bridge between the contact ring and a respective contact in the electrical outlet coupling when the cam is rotated to the closed position. A locking mechanism can be configured to selectively secure the medical lead in a fixed position relative to the housing when the cam is rotated to the closed position.

Another embodiment of the present disclosure provides a medical lead interconnect system including a housing, at least one plate, a biasing member, and a cam. The housing can include an electrical outlet coupling, and can define at least one channel shaped and sized to selectively receive an implantable medical lead. The at least one plate can be positioned within the housing, and can include a plurality of connector pins. The biasing member can be configured to bias the at least one plate away from the at least one channel. The cam can be configured to rotate between an open position, in which an implantable medical lead in insertable into the at least one plate, and a closed position in which the at least one plate is shifted to position the plurality of connector pins in contact with the implantable medical lead to create an electrical bridge between contact rings of the implantable medical lead and corresponding contacts of the electrical outlet coupling.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 8A is a partial, cross sectional view depicting a medical lead interconnect system and medical lead in an open position in accordance with an embodiment of the disclosure.

FIG. 8B is a partial, cross sectional view depicting the medical lead interconnect system and medical lead of FIG. 8A in a closed position.

FIG. 9A is a partial, cross sectional view depicting a medical lead interconnect system and medical lead in an open position in accordance with an embodiment of the disclosure.

FIG. 9B is a partial, cross sectional view depicting the medical lead interconnect system and medical lead of FIG. 9A in a closed position.

Figure 1:
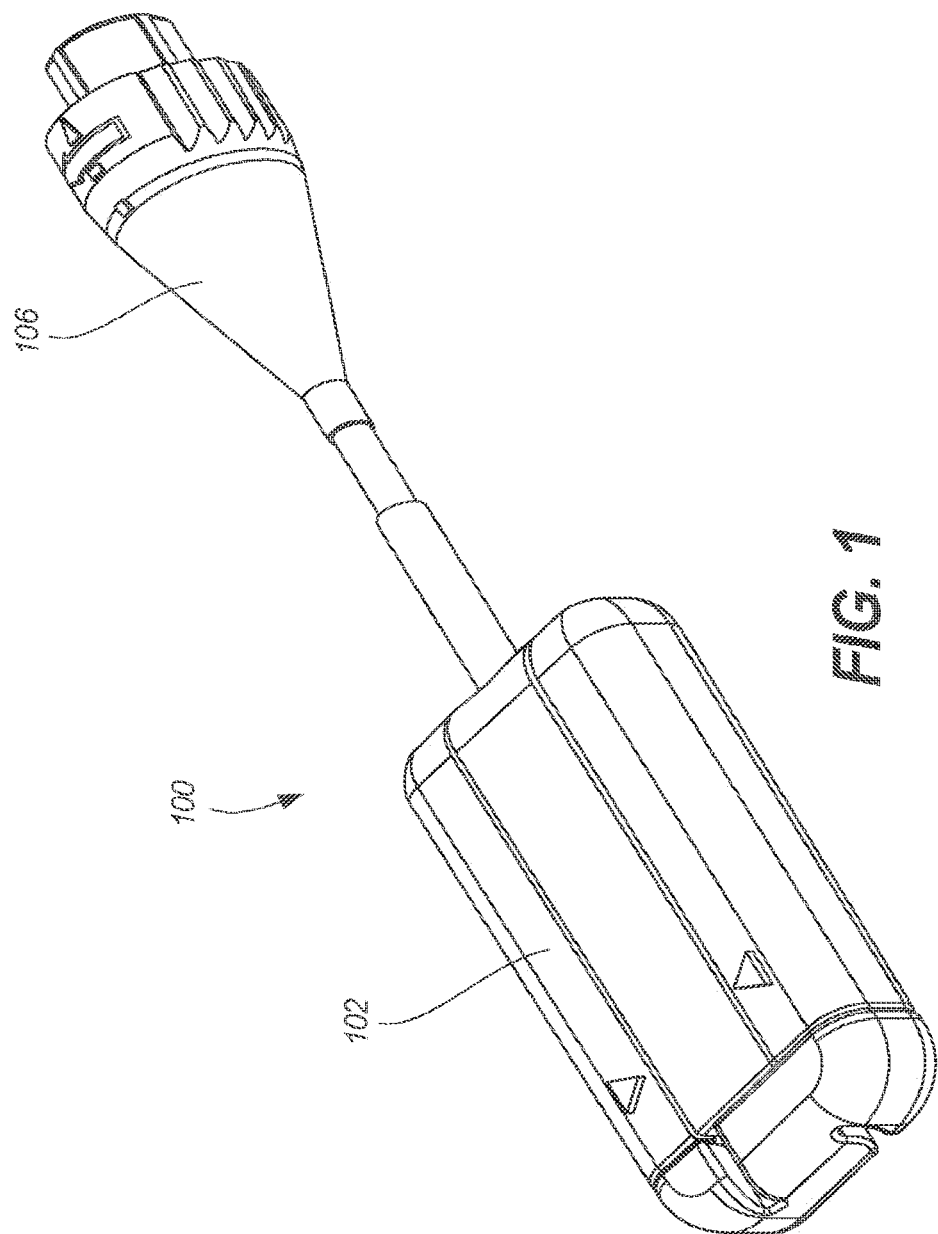
FIG. 1 is a perspective view depicting a medical lead interconnect system in accordance with an embodiment of the disclosure.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Figure 2:
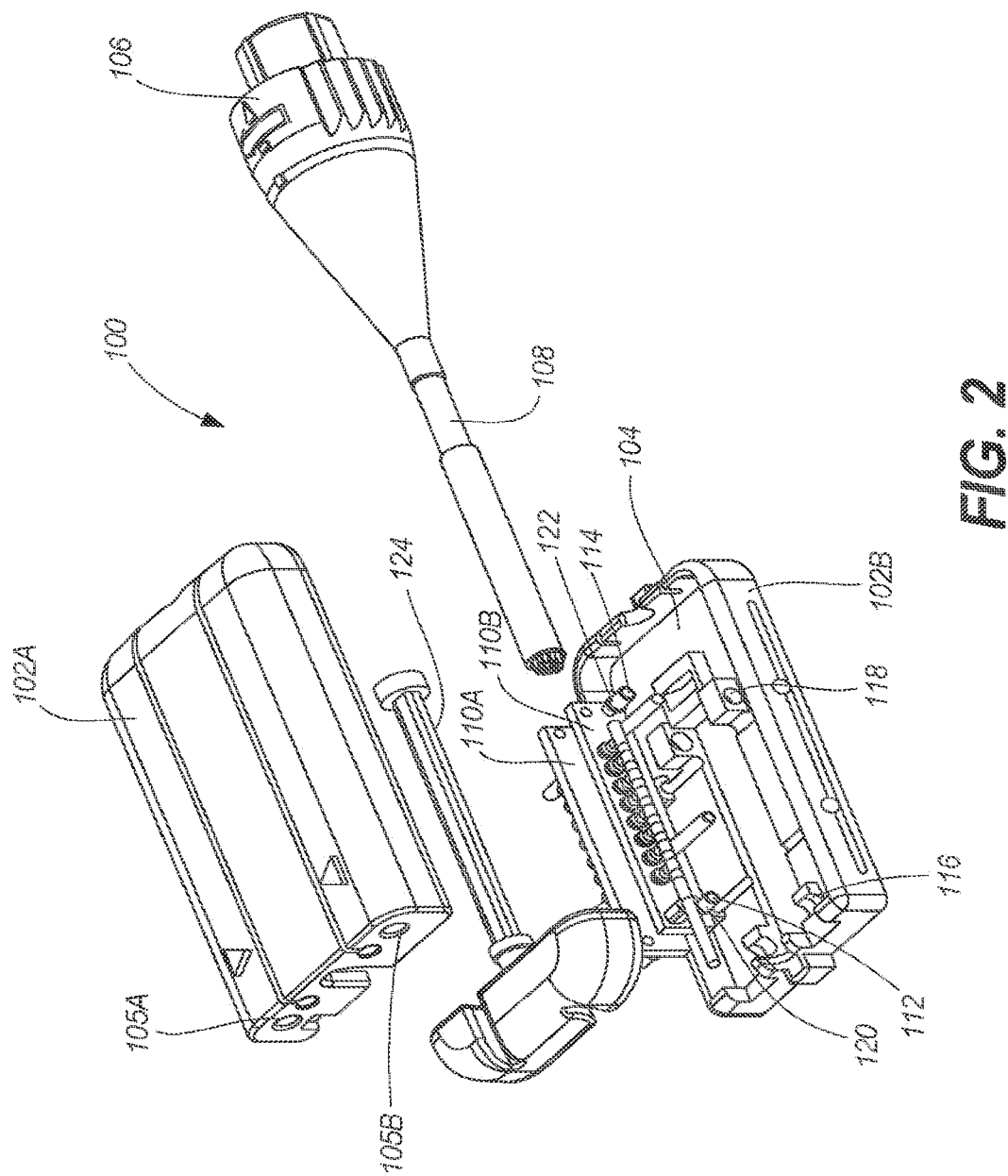
FIG. 2 is an exploded perspective view of the medical lead interconnect system of FIG. 1.
Figure 3A:
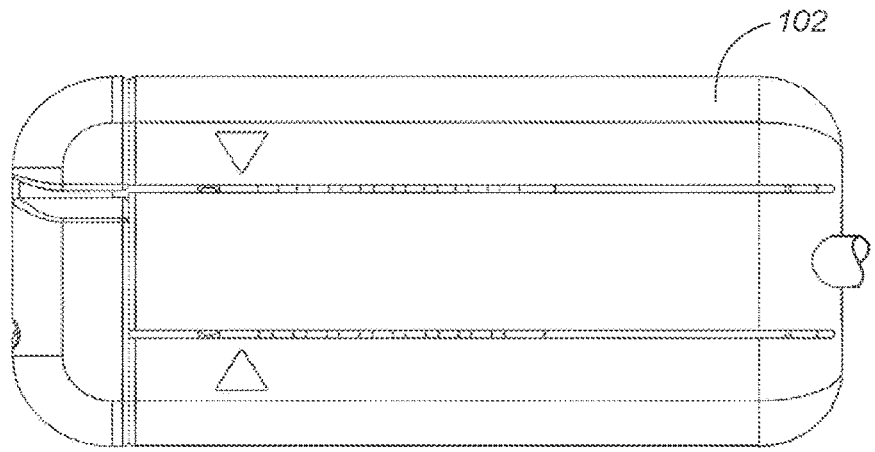
FIG. 3A is a top view depicting a housing in accordance with an embodiment of the disclosure.
Figure 3B:
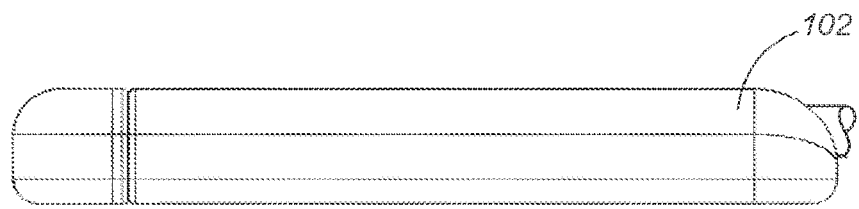
FIG. 3B is a side view depicting the housing of FIG. 3A.
Figure 3C:
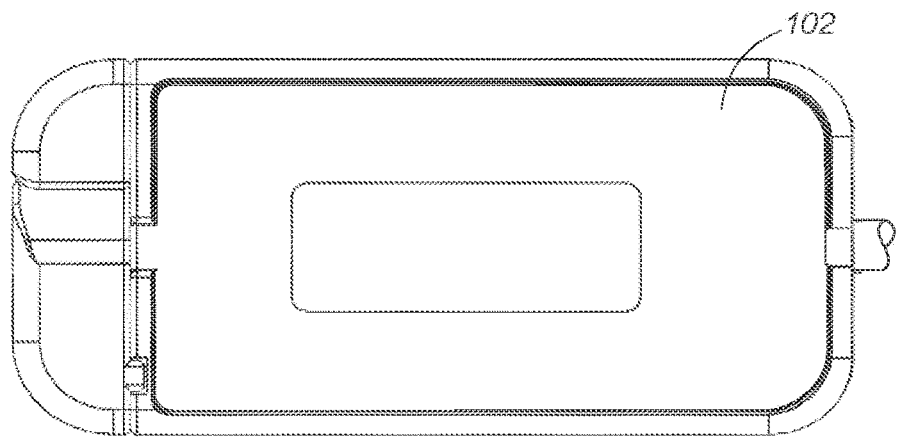
FIG. 3C is a bottom view depicting the housing of FIG. 3A.

Referring to FIGS. 1 and 2, a medical lead interconnect system 100 according to a disclosed embodiment is depicted. The medical lead interconnect system 100 can include a housing 102. Housing 102 can include a first portion 102A and a second portion 102B. Housing 102 can define an internal compartment 104 configured to house one or more internal components. In one embodiment, the housing 102 defines one or more apertures 105A/B, wherein each aperture 105 is shaped and sized to accept a medical lead 200. Additional views of housing 102 are depicted in FIGS. 3A-C.

An electrical outlet coupling 106 can be operably coupled to housing 102. For example, in one embodiment, electrical outlet coupling 106 can be coupled to housing 102 by a length of electrically conductive cable 108. Electrical outlet coupling 106 can be a standardized electrical coupling having 8- or 16-pins/receptacles, and can be configured to readily couple to its respective male or female counterpart. In one embodiment, electrical outlet coupling 106 can be a canon plug, or other plug configured to threadably couple to its respective male or female counterpart. In other embodiments, electrical outlet coupling 106 can couple to its respective male or female counterpart, and be held in place by friction interference.

One or more plates 110A/B can be positioned within housing 102. In one embodiment, each plate 110 can include a first pin 112 and a second pin 114. The first pin 112 and the second pin 114 can be configured to reside within a respective groove 116 and aperture 118 defined within the internal compartment 104 of housing 102, thereby enabling each plate 110 to shift orthogonally relative to the axis of the first and second pins 112, 114. In one embodiment, the medical lead interconnect system 100 can include a single plate 110. In another embodiment, the medical lead system 100 can include a pair of plates 110A/B.

In one embodiment, a biasing member 120, 122, such as a coil spring or other resilient member can be positioned proximal to the respective first and second pins 112, 114 so as to urge the one or more plates 110A/B in a particular direction along its shiftable path. For example, in one embodiment, the biasing members 120, 122 can bias plates 110A and 110B towards one another.

Figure 4A:
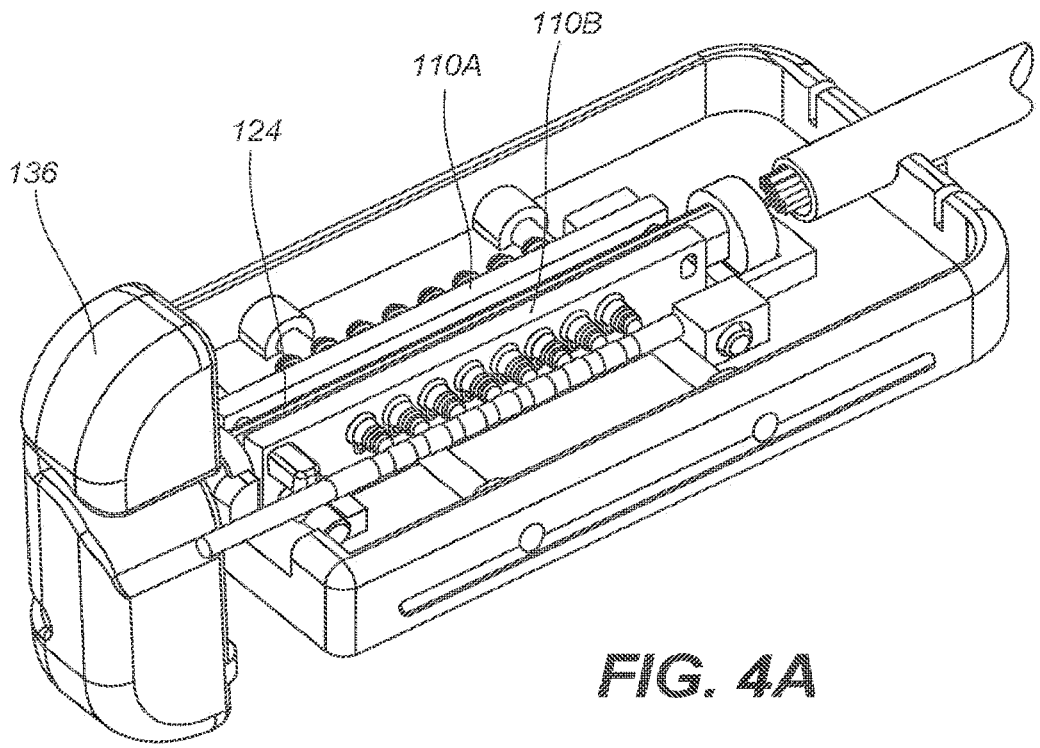
FIG. 4A is a cutaway perspective view depicting a medical lead interconnect system and medical lead in the open position in accordance with an embodiment of the disclosure.
Figure 4B:
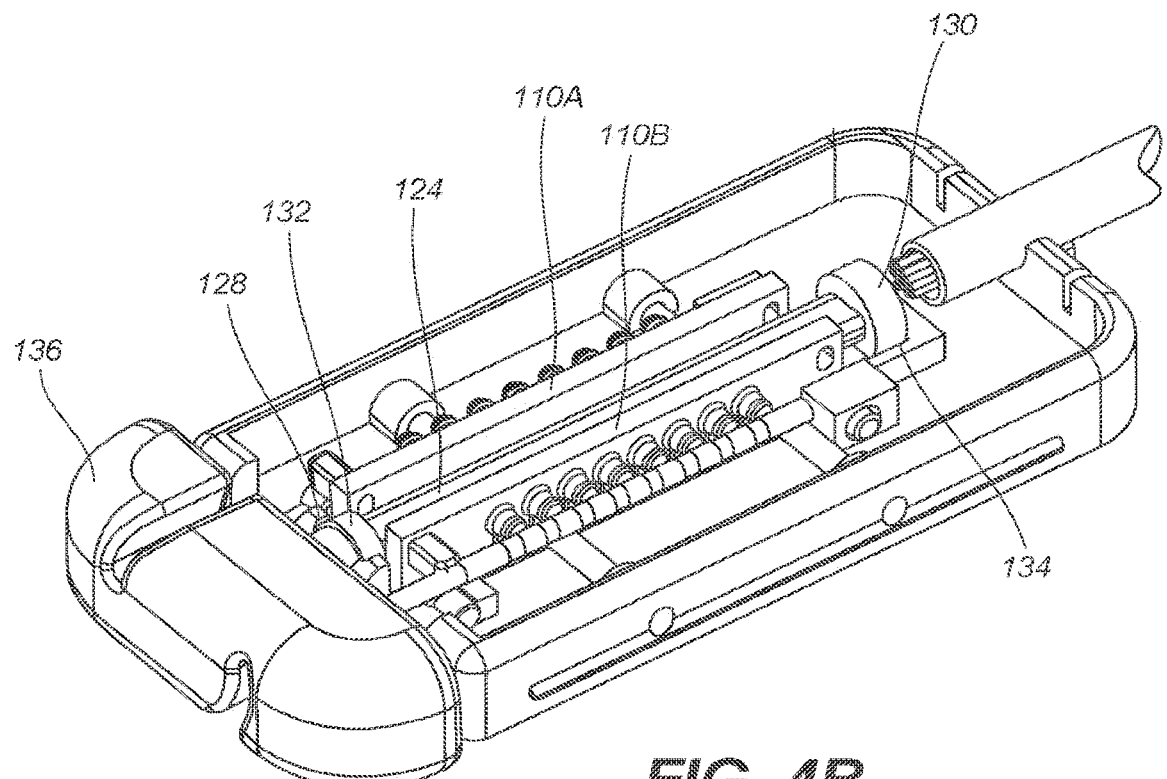
FIG. 4B is a cutaway perspective view depicting the medical lead interconnect system and medical lead of FIG. 4A in the closed position.

Referring to FIGS. 4A and 4B, a cam 124, can be positioned adjacent to one or more plates 110A/B within the internal compartment 104. For example, in one embodiment, cam 124 can be positioned between plates 110A/B. Cam 124 can be rotated between an open position (as depicted in FIG. 4A), in which the plates 110A and 110B are biased towards one another, and a closed position (as depicted in FIG. 4B), in which plates 110A and 110B are forced apart against the bias created by biasing member 120, 122. Cross-sectional views of cam 124 and plates 110A/B in the open and closed positions are depicted in FIGS. 8A-9B. In an embodiment with a single plate 110, cam 124 can be positioned between the plate 110 and a wall of housing 102.

Cam 124 can include a first cam mount 128 and a second cam mount 130. First and second cam mounts 128, 130 can be configured to reside within respective grooves 132, 134 defined within the internal compartment 104 of housing 102. At least one end of cam 124 can be operably coupled to a cam lever 136 extending from or positioned outside of housing 102.

Figure 5A:
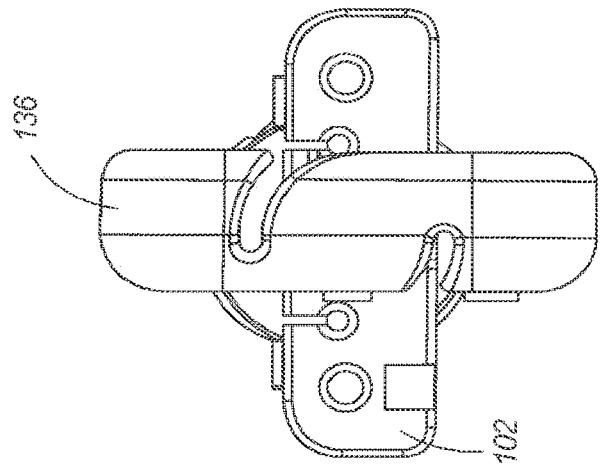
FIG. 5A is an end view depicting a medical lead interconnect system and medical lead in an open position in accordance with an embodiment of the disclosure.
Figure 5B:
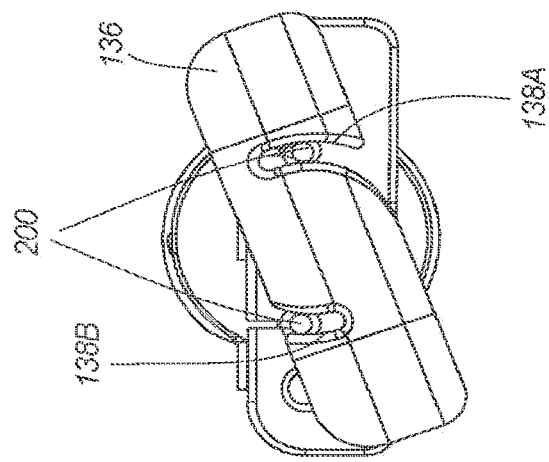
FIG. 5B is an end view depicting the medical lead interconnect system and medical lead of FIG. 5A in an intermediary position.
Figure 5C:
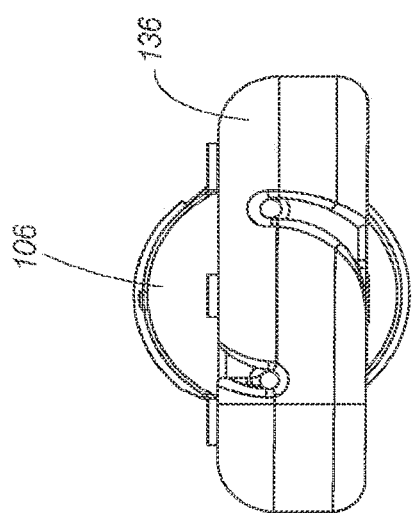
FIG. 5C is an end view depicting the medical lead interconnect system and medical lead of FIG. 5A in a closed position.

Referring to FIGS. 5A-C, cam lever 136 can define one or more curved channels 138A/B. Curved channels 138A/B can be sized and shaped to accommodate a portion of one or more leads 200, when rotating between the open position (as depicted in FIG. 5A), an intermediary position (as depicted in FIG. 5B), and a closed position (as depicted in FIG. 5C). In the closed position, the curved channels 138A/B can act to secure the one or more leads 200 in position relative to housing 102, thereby inhibiting movement of one or more leads 200. Accordingly, in one embodiment, the one or more curved channels 138A/B serve as a first locking mechanism configured to selectively secure the medical lead in a fixed position relative to the housing 102 when the cam 124 is rotated to the closed position. In one embodiment, cam lever 136 can pivot about an axis positioned between a pair of apertures 105A/B.

Figure 6:
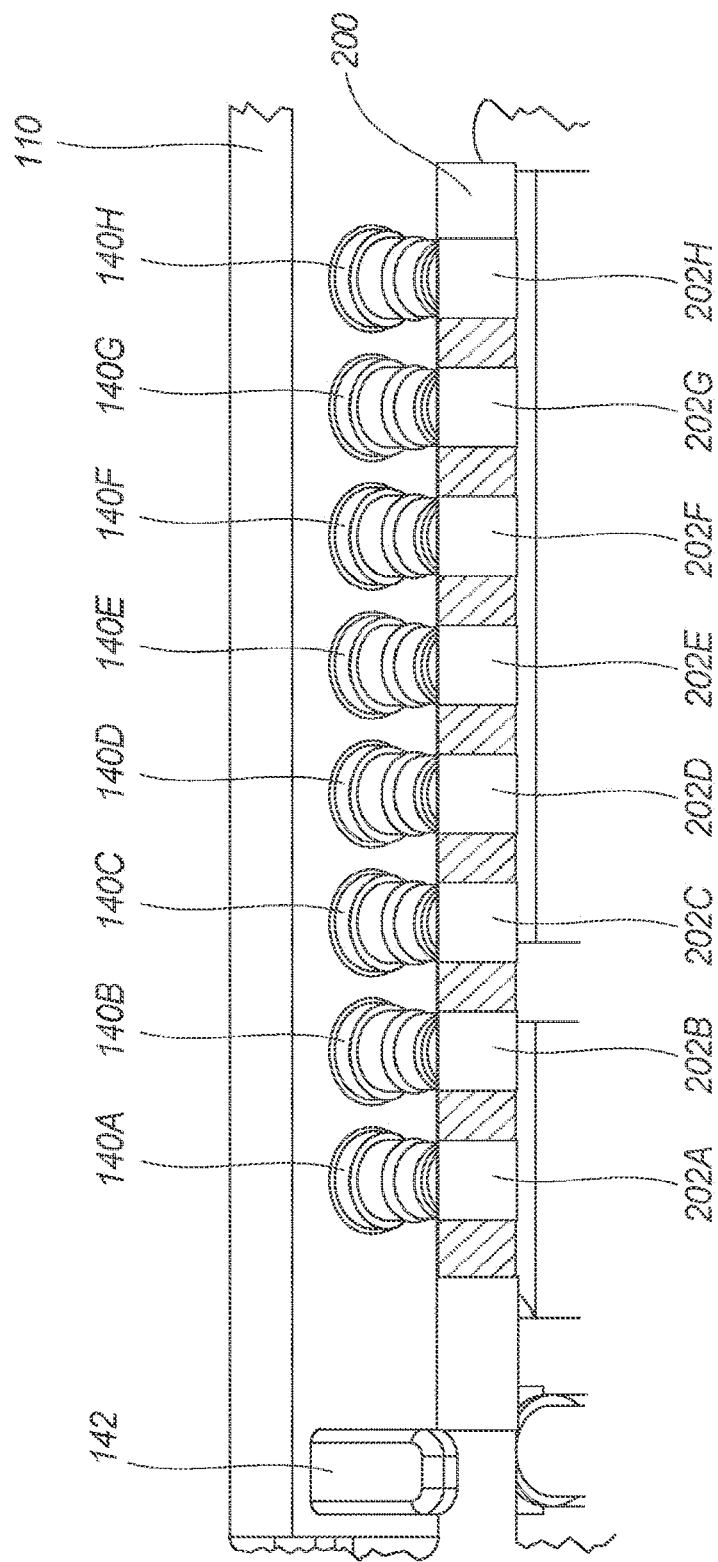
FIG. 6 is a close-up, partial view depicting a plate and medical lead in accordance with an embodiment of the disclosure.

Referring to FIG. 6, each plate 110 can have a length corresponding to the dimension of a linear array of contacts 202 of a medical lead 200. Along said length, each plate 110 can include one or more connector pins 140A-H, and one or more wedge 142. In one embodiment, each of the connector pins 140A-H corresponds to a contact ring 202A-H of the medical lead 200 to selectively create an electrical bridge between the contact ring 202A-H and a respective contact in the electrical outlet coupling 106 when the cam 124 is rotated to the closed position. Individual cables within electrically conductive cable 108 can couple the connector pins 140A-H to the respective contacts in the electrical outlet coupling 106. In one embodiment, the connector pins 140 can include a resilient member, such as a spring, to improve electrical contact with the contact rings 202 of the medical lead 200.

The wedge 142 can be configured to selectively secure the medical lead 200 in a fixed position relative to the housing 102 when the cam 124 is rotated to the closed position. Accordingly, in some embodiments, the medical lead interconnect system includes a first locking mechanism (e.g., the curved channels 138 of cam lever 136) and a second locking mechanism (e.g., wedge 142).

Figure 7A:
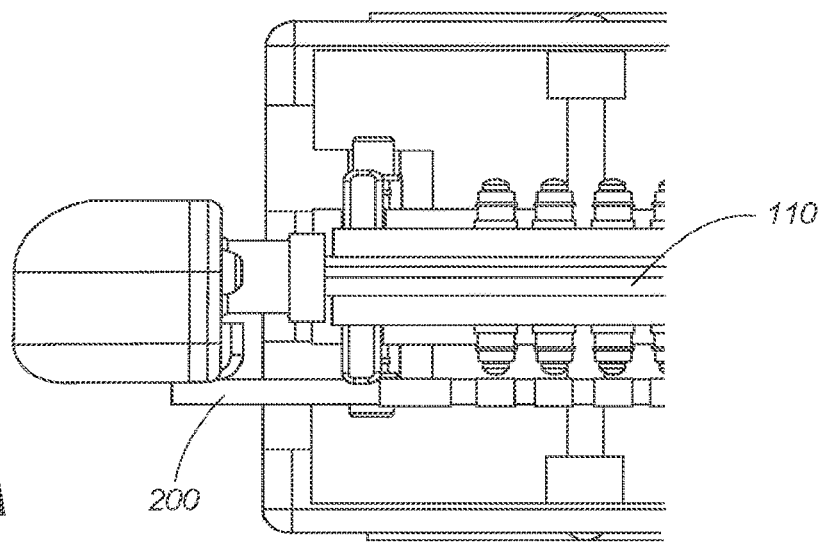
FIG. 7A is a partial, cutaway plan view depicting a medical lead interconnect system and medical lead in an open position in accordance with an embodiment of the disclosure.
Figure 7B:
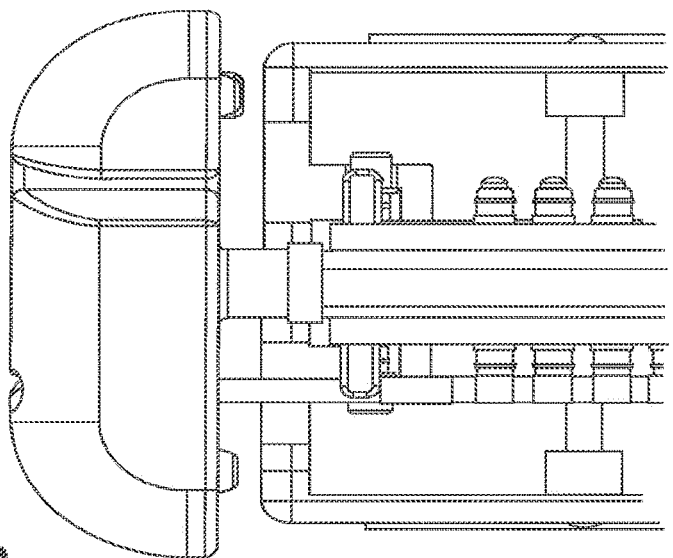
FIG. 7B is a partial, cutaway plan view depicting the medical lead interconnect system and medical lead of FIG. 7A in a closed position.

Referring to FIGS. 7A-9B, in operation, when the medical lead interconnect system 100 is in the open position (as depicted in FIGS. 7A, 8A and 9A), one or more medical leads 200 can be inserted into the internal compartment 104 of housing 102, so that the medical lead 200 parallels plate 110. In one embodiment, the one or more medical leads 200 can be inserted into the housing 102 with little or no resistance, as the connector pins 140 and the wedge 142 are shifted out of the path of the one or more medical leads 200, so as to not create any frictional interference. With the one or more medical leads 200 fully inserted, the cam lever 136 can be rotated to the closed position (as depicted in FIGS. 7B, 8B and 9B). In the closed position, the cam 124 forces plates 110A/B apart from one another against the bias of biasing member 120, 122, thereby shifting plates 110A/B within housing 102 towards the one or more medical lead 200. As plates 110A/B shift towards the one or more medical leads 200, the connector pins 140A-H and wedge 142 contact the one or more medical lead 200, such that each of the connector pins creates an electrical bridge between the respective contact ring 202A-H on the one or more medical lead 200 and a contact in the electrical outlet coupling 106, and the wedge 142 contacts the one or more medical lead 200 to hold the medical lead 200 in a fixed position relative to housing 102. The curved channels 138 of cam lever 136 can further aid in securing the position of the one or more medical lead 200 relative to housing 102.

The one or more medical lead 200 can be removed or uncoupled from the medical lead interconnect system 100 by reversing the above procedures.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A medical lead interconnect system configured to selectively electrically couple a linear array of contact rings of an implantable medical lead to an electrical outlet coupling, the medical lead interconnect system comprising:
   a housing including the electrical outlet coupling;
   a pair of plates positioned within the housing, each plate having a plurality of connector pins;

a biasing member configured to bias the pair of plates towards one another; and a cam configured to rotate between an open position in which the pair of plates positioned in proximity to one another, and a closed position in which the pair of plates are shifted apart from one another by contact from the rotated cam thereby shifting against the bias of the biasing member, wherein each of the plurality of connector pins are configured to contact a corresponding contact ring of the linear array of contact rings of the implantable medical lead to selectively create an electrical bridge between the contact ring and a respective contact in the electrical outlet coupling when the cam is rotated to the closed position.

2. The medical lead interconnect system of claim 1, wherein a first locking mechanism is configured to selectively secure the medical lead in a fixed position relative to the housing when the cam is rotated to the closed position.

3. The medical lead interconnect system of claim 2, wherein a cam lever is operably coupled to the cam.

4. The medical lead interconnect system of claim 3, wherein the cam lever defines a pair of curved channels, each curved channel shaped and sized to accommodate a portion of the implantable medical lead to inhibit movement of the implantable medical lead when the cam is rotated to the closed position.

5. The medical lead interconnect system of claim 4, wherein the first locking mechanism comprises the pair of curved channels.

6. The medical lead interconnect system of claim 5, wherein a second locking mechanism comprises a wedge coupled to the pair of plates.

7. The medical lead interconnect system of claim 1, wherein the electrical outlet coupling is a standardized electrical coupling having at least eight receptacles.

8. The medical led interconnect system of claim 1, wherein the electrical outlet coupling is a standardized electrical coupling having at least sixteen receptacles.

9. The medical lead interconnect system of claim 1, wherein the electrical outlet coupling is threadably couplable to a respective counterpart.

10. The medical lead interconnect system of claim 1, wherein the electrical outlet coupling is frictionably couplable to a respective counterpart.

11. The medical lead interconnect system of claim 1, wherein each plate of the pair of plates shifts between the open and closed positions substantially orthogonal to a central axis of the implantable medical lead.

12. The medical lead interconnect system of claim 1, wherein each of the plurality of connector pins includes a resilient member to improve electrical contact with the contact rings of the implantable medical lead.

13. The medical lead interconnect system of claim 1, wherein each plate of the pair of plates can include a wedge configured to selectively secure the medical lead in a fixed position relative to the housing when the cam is rotated to the closed position.

14. A medical lead interconnect system, comprising:
a housing including an electrical outlet coupling and defining at least one aperture shaped and sized to selectively receive an implantable medical lead;
at least one plate positioned within the housing, and including a plurality of connector pins;
a biasing member configured to bias the at least one plate away from the at least one aperture; and
a cam configured to rotate between an open position in which an implantable medical lead is insertable into the at least one aperture without interference by the plurality of connector pins of the at least one plate, and a closed position in which the at least one plate is shifted via contact from the cam to position the plurality of connector pins in contact with the implantable medical lead to create an electrical bridge between contact rings of the implantable medical lead and corresponding contacts of the electrical outlet coupling.

15. The medical lead interconnect system of claim 14, wherein a first locking mechanism is configured to selectively secure the medical lead in a fixed position relative to the housing when the cam is rotated to the closed position.

16. The medical lead interconnect system of claim 14, wherein a cam lever is operably coupled to the cam.

17. The medical lead interconnect system of claim 16, wherein the cam lever defines a pair of curved channels, each curved channel shaped and sized to accommodate a portion of the implantable medical lead to inhibit movement of the lead when the cam is rotated to the closed position.

18. The medical lead interconnect system of claim 17, wherein the first locking mechanism is the pair of curved channels.

19. The medical lead interconnect system of claim 18, wherein a second locking mechanism comprises a wedge coupled to the pair of plates.

* * * * *